United States Patent [19]
Wajid

[11] Patent Number: 5,524,477
[45] Date of Patent: Jun. 11, 1996

[54] QUANTITATIVE DETERMINATION OF AIR PRESENT IN REFRIGERANT SAMPLE BY MEASUREMENT OF PRESSURE COEFFICIENT OF RESONANCE FREQUENCY

[75] Inventor: Abdul Wajid, East Syracuse, N.Y.

[73] Assignee: Leybold Inficon Inc.

[21] Appl. No.: 190,306

[22] Filed: Feb. 2, 1994

Related U.S. Application Data

[63] Continuation-in-part of Ser. No. 158,562, Nov. 29, 1993.

[51] Int. Cl.$^6$ ................................................. G01N 29/12
[52] U.S. Cl. ........................... 73/24.05; 73/24.01; 73/579
[58] Field of Search .................................. 73/23.2, 24.01, 73/24.06, 24.04, 24.05, 31.05, 579, 597

[56] References Cited

U.S. PATENT DOCUMENTS

| | | | |
|---|---|---|---|
| 2,653,471 | 9/1953 | Clewell | 73/24.01 |
| 3,434,334 | 3/1969 | Vandenbussche | 73/24.01 |
| 3,468,157 | 9/1969 | Burk et al. | 73/24.01 |
| 3,544,276 | 12/1970 | Merwitz | 73/28.01 |
| 3,762,197 | 10/1973 | Roof et al. | 73/24.01 |
| 4,212,201 | 7/1980 | Hirsch et al. | 73/579 |
| 4,255,964 | 3/1981 | Morison | 73/24.01 |
| 4,280,183 | 7/1981 | Santi | 73/24.01 |
| 4,679,947 | 7/1987 | Miller et al. | 73/24.04 |
| 4,939,905 | 7/1990 | Manz | 62/77 |
| 5,060,506 | 10/1991 | Douglas | 73/24.01 |
| 5,076,094 | 12/1991 | Frye et al. | 73/19.03 |
| 5,158,747 | 10/1992 | Manz et al. | 73/24.04 |
| 5,159,843 | 11/1992 | Shakkottai et al. | 73/24.05 |
| 5,386,714 | 2/1995 | Dames | 73/24.05 |

*Primary Examiner*—Hezron E. Williams
*Assistant Examiner*—Rose M. Finley
*Attorney, Agent, or Firm*—Harris Beach & Wilcox

[57] ABSTRACT

An acoustic technique is employed to identify the species of a refrigerant gas and whether it contains significant contaminants. Air in the refrigerant can be tolerated, but must be accounted for in determining the acoustic properties of the sample. The refrigerant is admitted into a Helmholtz resonator under a controlled pressure, and a drive frequency is applied to a transducer. Another transducer picks up the vibrations in the resonator and an output signal is compared to the drive signal to find resonant peaks and sharpness factors. The change in resonant frequency with pressure is measured, and is employed to quantify the presence of air in the sample. The amount of air present determines a frequency correction, which permits unambiguous identification of the species of refrigerant and of its purity.

5 Claims, 8 Drawing Sheets

QUANTITATIVE DETERMINATION OF AIR PRESENT IN REFRIGERANT SAMPLE BY MEASUREMENT OF PRESSURE COEFFICIENT OF RESONANCE FREQUENCY

This is a continuation-in-part of U.S. patent application Ser. No. 08/158,562 filed Nov. 29, 1993 still pending.

BACKGROUND AND SUMMARY OF THE INVENTION

The invention relates to a method and apparatus for identifying a gaseous substance and determining its purity, using acoustic techniques. The invention is more particularly concerned with identification of a gaseous substance of unknown species by analysis of frequency response of a resonator containing the substance in vapor form. The invention is more specifically concerned with detection of a significant air mass in a charge of refrigerant, as may occur in the case of a leak in an air conditioning system, and also with accounting for the presence of such air when carrying out an analysis of a test refrigerant for species and purity.

In the field of air conditioning service and repair, there is a need to identify the refrigerant charge contained in a system so that the refrigerant can be properly handled for reclamation and recycling, or for disposal. In recent years, because of environmental concerns, it has become the practice for air conditioner repair shops to capture and retain the used refrigerant in a reclamation system, rather than permit it to escape into the atmosphere. Also, because of the high cost of disposal of unresuable refrigerant, and because of the high cost of fresh refrigerant, economic needs have also driven air conditioner repair shops to reclaim the refrigerant charge in a reclaimer device provided for that purpose.

For similar environmental concerns, manufacturers of automotive air conditioning systems have begun to switch over from type R12 refrigerant (dichloro-difluoro methane) to another refrigerant, R134A (1,1,1,2-tetrafluoroethane) which is believed to be gentler to the environment than R12 if it escapes to the atmosphere. Type R134A refrigerant was engineered to have thermal characteristics very similar to R12 refrigerant so that R134A based systems could be used where R12 systems are now used, i.e., in automotive air conditioning systems. On the other hand, R134A refrigerant is chemically incompatible with R12 refrigerant, and cannot be reused if one refrigerant is contaminated with the other. Also, if either refrigerant R12 or R134A has been contaminated with another refrigerant such as R22, the refrigerant should not be reused. However, if the refrigerant contains air or lubricant, the refrigerant can be deemed acceptable, because the reclaiming device can remove these impurities from the refrigerant.

Techniques of identifying a species of a fluid by means of its dielectric properties have been described e.g. in U.S. Pat. Nos. 5,150,683; 5,091,704; and 5,119,671. For example, the relative percentages of a gasoline/alcohol fuel mixture are measured by applying an RF signal to a coil submerged in the mixture. This system would not be workable for identifying which of two refrigerant species is present, or if unacceptable contaminants are present in the refrigerant.

A technique to identify and distinguish between two different refrigerant gases, based on the dielectric properties of the gases, it described in U.S. Pat. No. 5,158,747. The device of that patent can also be configured to be responsive to acoustic properties of the refrigerant vapor, by sensing changes in velocity or phase angle of acoustic waves traveling in the refrigerant vapor. However, this type of device is not precise enough to sense whether impurities are present in unacceptable levels.

The refrigerant can be tested by introducing a sample of it, in vapor form, into a resonant chamber, which in the preferred mode is a Helmholtz resonator, at a controlled vapor pressure, e.g., 2.25 psig. A Helmholtz resonator has the beneficial property of providing resonances at frequencies of a few hundred hertz in a unit of very compact size. The Helmholtz resonator can also be constructed so as to have plural resonances, if desired. In one preferred mode, the resonant chamber is formed to produce two distinct resonances, and in the preferred construction the Helmholtz resonator has first and second necks, each of a respective length and area, connecting first and second volumes. A frequency generator produces a sweep of frequencies in a band that includes the two resonances, and this sweep is applied to a transducer in one of the first and second volumes. Another transducer, responsive to vibrations in the resonant chamber, produces an output signal that varies in response to the amplitude of the vibrations in the chamber. A digital circuit responsive to the frequency generator and second transducer output determines the center frequencies for the first and second resonances and also determines the frequency width of these resonances to yield quality or sharpness factors for the two resonances. Then these center frequencies and sharpness factors are compared with stored data concerning two or more candidate species of the refrigerant, and a determination is made as to the identity of the refrigerant species of the sample, and the extent and nature of any contaminants.

A thermal sensor in contact with the chamber is coupled to the digital circuit so that it can compensate for any temperature variations. The chamber is isolated from external environmental noise.

A regulator at the chamber inlet regulates vapor pressure at the sample gas to a predetermined level, for example, at 2.25 psig. The regulator also permits the chamber to be evacuated to twenty nine inches of mercury below ambient.

The device performance is entirely satisfactory when refrigerants are pure or cross contaminated (i.e., R12/R134A mixtures). The device can also determine the presence of a large quantity of air in the system, as can happen when there is a leak in the system.

However, a small fraction of air, i.e., between 2% and 20% air, in R12 refrigerant can be mistaken as contamination by R134A. Thus, the presence of a small quantity of air can prevent the device from providing an unambiguous result unless all air is somehow paired from the system. In principle, a properly charged air conditioning system should not contain any air mass in the refrigerant. However, in practice many automotive air conditioning systems do contain a small quantity of air throughout the system, or accumulated near the test ports. This can occur for a variety of reasons, such as compressor design problems, or improper purging of the system prior to charging.

Accordingly, it is desired to circumvent the air contamination problem by simple process steps that can be carried out with the refrigerant test equipment described just above, and which will automatically adjust for the air, if any, that is present in the refrigerant charge being tested.

It is therefore an object of this invention to provide a technique for automatically determining the quantity of air present in a refrigerant charge.

It is another object to provide a technique for unambiguously identifying the species and purity of a sample of a refrigerant vapor, and to account for the presence of air therein, employing acoustical techniques.

According to an aspect of this invention, a technique can be employed to circumvent the problem of air contamination in refrigerant gases. A Helmholtz resonator, or other equivalent resonator chamber, can be employed with a technique somewhat different from that described above. By operating the resonance chamber at two different predetermined pressures, a secondary parameter is derived which is directly related to the percentage of air present in the air conditioning system. Then, by subtracting the effect of the air present on the resonance frequency, a corrected resonant frequency is derived. This corrected resonant frequency can be analyzed to discriminate between refrigerants.

In particular, the resonant test call (or Helmholtz resonator) is purged and then filled with the vapor to be tested, up to a predetermined pressure $P_2$ which can be on the order of about 10 psig. This can be carried out with a combination of a pressure sensor and a bleed valve, or through a bistable regulator. A transducer in contact with the vapor in the resonator, and the principal resonance frequency $F_2$ is found. Then vapor is gradually evacuated from the resonator until a lower pressure $P_1$ is reached. This can be about 0.25 psig. Then the resonance frequency $F_1$, is found for this pressure $P_1$.

The slope S of the normalized frequency curve is found, indicating the change of frequency with pressure. For this, the relationship is employed:

$$S=(F_2/F_1-1)/(P_2-P_1)$$

The value of the slope S is compared with previously calibrated values or with a calibration curve to identify the percent of air in the refrigerant sample.

From this value, the expected frequency shift for the given quantity of air present can be determined, referring to other pre-calibrated reference values or to another calibration curve. This frequency shift can be subtracted from the frequency $F_1$ to determine a corrected resonance frequency. The species and purity of the sample gas can be determined using the corrected resonance frequency.

In some cases a two resonance chamber can be used, and two pairs of resonant frequencies can be measured, one pair at each pressure $P_1$ and $P_2$. It is also possible to measure resonant frequencies for three or more pressure values, thus increasing the accuracy of the calculation of the slope factor S.

The above and many other objects, features, and advantages of this invention would present themselves to persons skilled in the art from a reading of the ensuing description of a preferred embodiment, to be read in connection with the accompanying Drawing.

DETAILED DESCRIPTION OF THE DRAWING

Figure 1:
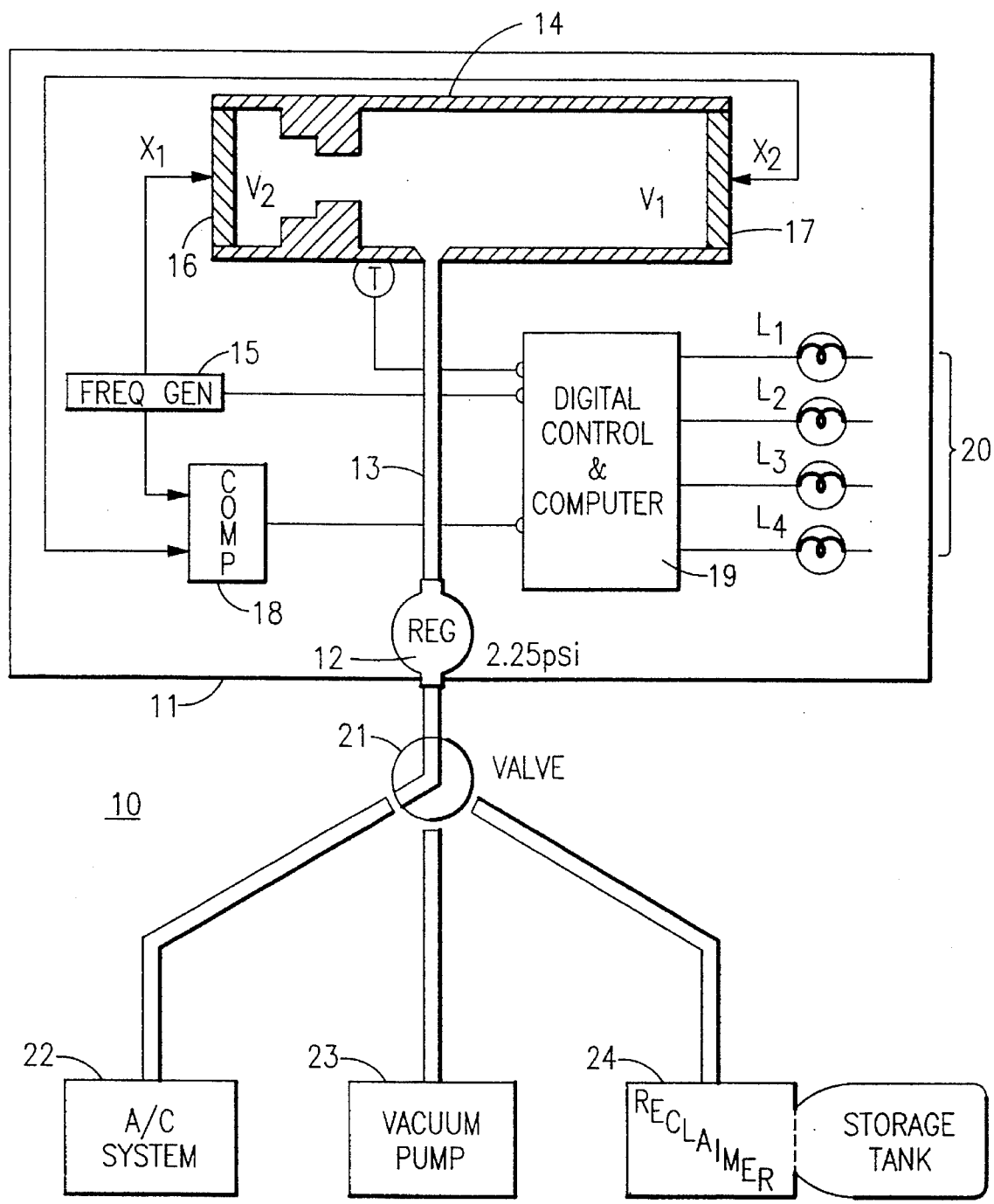
FIG. 1 is a system schematic of a refrigerant interrogation device in which the technique of this invention can be practiced.

With reference to the Drawing, and initially to FIG. 1, a refrigerant interrogation device 10 is configured to assess the species of a refrigerant gas and the refrigerant's purity. The principle of its operation is to utilize information that is derived by measuring the unknown gas' acoustic properties.

The measured data about the unknown sample gas physical parameters are then compared with stored, predetermined knowledge bases of the acoustical properties of two or more likely candidate refrigerants, and mixtures thereof. In addition to knowledge of the acoustic properties of various pure refrigerant gases, the technique of this invention also employs knowledge of the acoustic behavior of the target refrigerants in mixtures. The decision as to refrigerant species and purity can be made on the basis of any of several algorithms, and one successful technique utilizes logical values and best fit.

In the device 10 shown in FIG. 1, a housing 11 contains equipment beginning with an inlet regulator 12 that is coupled by a gas conduit 13 to a Helmholtz resonator 14, to be described briefly below. A frequency generator 15 generates a sweep of frequencies across a spectrum from about 300 Hz to about 3000 Hz, and applies the sweep of frequencies to an electroacoustic transducer or microphone 16 that is in contact with an interior volume $V_2$ of the resonator 14. A pickup transducer or microphone 17 in contact with another interior volume $V_1$ of the resonator senses vibrations in the volume $V_1$. This transducer 17 provides an output signal to a comparator 18. The comparator also receives the driving signal from the generator 15.

Each transducer 16, 17 has an associated diaphragm in the form of a foil or membrane to isolate the microphone from the sample within the resonator. The diaphragms are tensioned and vacuum-tight. The foils or membranes protect the transducers from refrigerants that can be chemically active, and also protect the transducers from overpressure.

The frequency generator 15 provides a precision, frequency-variable drive signal for acoustically exciting the resonator 14. The generator is rapidly alterable in frequency to a precision of about 0.1 Hz. The comparator 18 then provides a sensitive and precise means of acoustic energy level detection, with sufficient resolution to identify resonant peaks to within about 0.1 Hz. The comparator 18 can operate, for example, on the basis of phase shifts as between the drive signal and pickup signal.

A digital control and computer 19 has an input coupled to the comparators 18 and a control output coupled to the generator 15. A temperature detector 20 in thermal communication with the resonator 14 provides a temperature signal to the digital control and computer 19. Based on the results of the test conducted with a given sample, the computer 19 will activate one of a group of indicator lamps or LEDs L1, L2, L3. These can be configured so that if the sample is identified as R12, lamp L1 is lit, or if the sample is identified as R134A, lamp L2 is lit. If the sample contains an unacceptable level of an adulterant, such as another refrigerant, the lamp L3 is lit. Another lamp or LED L4 can be provided to indicate that a test is in progress. An additional lamp can indicate, for example, that the cell has not been properly purged between uses, or that the sample contains air or another light gas such as propane.

Also shown in FIG. 1, the device 10 can be coupled via a selector valve 21 to each of an air conditioner, refrigerator, or heat-pump system 22, a vacuum pump 23, and a reclaimer device 24, each of which can be of any standard configuration. The regulator 12 permits the vacuum pump 23 to purge residual gases from the resonator 14 down to twenty nine inches of mercury. The system 22 typically provides a refrigerant pressure of between about 35 to 400 psi, and the regulator 12 reduces this pressure to about 2.25 psi before admitting a sample of the refrigerant into the interior of the resonator.

The sample is tested, and if it is identified as a particular refrigerant without unacceptable levels of contaminants, the valve 21 can rotate so that the refrigerant charge from the air conditioner system 22 is supplied to the reclaimer device 24 for purging and storage. If the charge is identified as a refrigerant mixture or a refrigerant with an unacceptable contaminant level, the charge can be directed to a holding tank (not shown) for later disposal.

The resonator 14 shown in FIG. 1 is of the Helmholtz type, having first and second large volumes $V_1$, $V_2$, that are connected by a pair of necks 25, 26, here arranged in series. Each of the necks has a predetermined length $l_1$, $l_2$ and a predetermined cross sectional area $A_1$, $A_2$.

Helmholtz resonators have natural frequencies $F_H$ that depend on the dimensions of the neck 25, 26 and the speed of sound $C_o$ of the gas in the chamber. The general formula for the principal resonance frequency is $$(2\pi)^2 F_H^2 = C_o^2 \frac{A}{vl}$$

where $l$ and $A$ are the length and area of the neck, and $v$ is the effective volume, $v=1\div(1/V_1+1/V_2)$.

The resonator 14 with the two necks 25, 26 will produce a pair of resonances $f_1$ and $f_2$. The volumes $V_1$, $V_2$ neck lengths $l_1$, $l_2$ and neck areas $A_1$, $A_2$ are fixed parameters, so the Helmholtz resonances $f_1$ and $f_2$ depend only on the speed of sound $C_o$ of the refrigerant gas.

Figure 2:
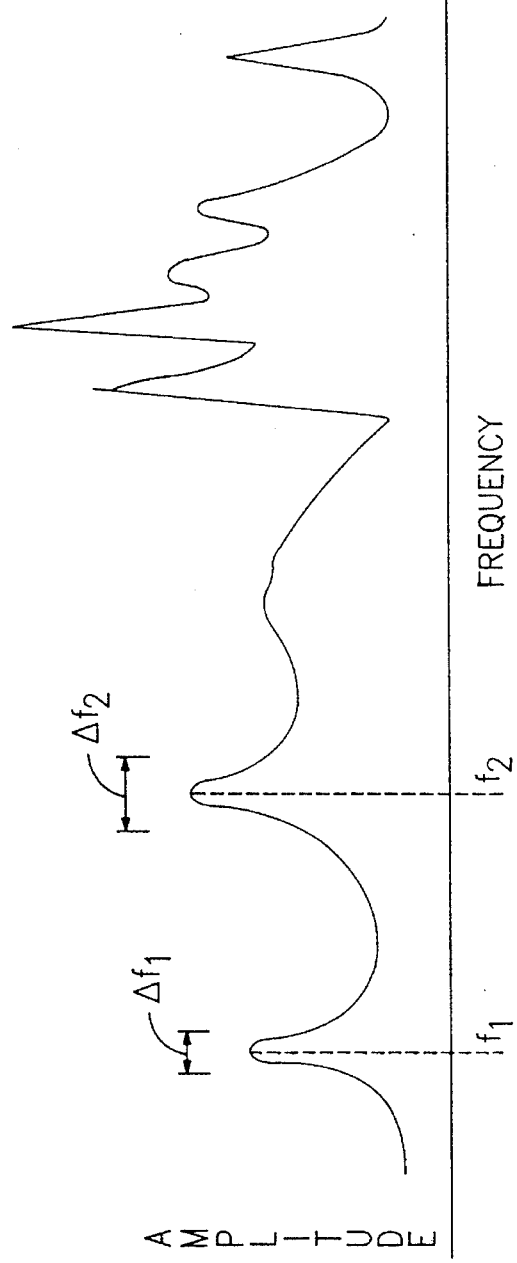
FIG. 2 is a chart showing the positions and sharpness of the resonances of the vapor within the test cell of the interrogation device.

FIG. 2 shows a typical resonance curve, in the frequency domain, for the Helmholtz resonator 14 containing an unknown sample refrigerant. The two necks 25, 26 produce resonance peaks with respective peak or center frequencies $f_1$, $f_2$. Because of impurities in the sample, the resonances can vary in half-peak frequency width, here identified as $\Delta f_1$ and $\Delta f_2$. As is commonly understood these data provide a quality figure Q or resonance sharpness factor for each resonance, namely, $$Q_1 = \frac{f_1}{\Delta f_1} \qquad Q_2 = \frac{f_2}{\Delta f_2}$$

The resonances at the high-frequency end of the chart can be disregarded for these purposes.

In the technique of this invention, the frequency generator 15 drives the first transducer 16 with a sine wave of precise amplitude and frequency. An initial sweep is carried out at a fast rate to locate the approximate positions of the two resonances in the frequency domain. Then in the neighborhood of each of the resonances, the sweep of frequencies is carried out at a slower, more precise rate to identify the peak frequencies $f_1$ and $f_2$ and to measure the frequency half-widths $\Delta f_1$ and $\Delta f_2$. The frequencies and frequency half-widths are corrected to compensate for any temperature fluctuations.

Using the resonance frequencies $f_1$, $f_2$ and the sharpness or quality figures $Q_1$, $Q_2$, a value can be found for the equivalent inertial mass, $m'$, of the refrigerant vapor.

For this, each of the two resonances can be considered as a driven harmonic oscillator, where displacement, x, of the gas within each of the necks 25, 26 can be expressed in the equation.

$$m'\frac{d^2x}{dt^2} + Kx + 2\gamma\frac{dx}{dt} = A_o\cos 2\pi ft$$

where K is an equivalent spring constant, $\gamma$ is a damping factor, and $A_o$ is the amplitude of the driving frequency, which is considered a constant.

From elementary mechanics, it is understood that the natural resonance frequency F is $$F = \frac{1}{2\pi}\sqrt{\frac{K}{m'}}$$

while the damping factor $\gamma$ is related to the resonance sharpness Q according to the relationship $$\frac{\gamma}{m'} = \frac{2\pi F}{Q}$$

This leads to $$\frac{d^2x}{dt^2} + 4\pi^2 F^2 x + \frac{4\pi F}{Q}\frac{dx}{dt} = A_o\cos 2\pi Ft$$

In steady state, this yields $X(t)=X_o\cos(2\pi ft+\delta)$.

Here $\delta$ is a phase angle given by $$\tan\delta = -\frac{fF/Q}{F^2 - f^2}$$

The amplitude $X_o$ of the detected oscillations in the resonator is given by $$X_o(f) = \frac{A_o/m}{\sqrt{((2\pi F)^2 - (2\pi f)^2)^2 - (4\pi^2 Ff/Q)^2}}$$

Thus for each gas there is a set of resonance characteristics, namely a resonance frequency F, a quality factor (i.e. Q), and an effective mass $m'$.

This is also true for mixtures of the various refrigerants.

Within the digital control and computer 19 there are stored resonance behavior data for various refrigerants, e.g., R12, R22, and R134A, and mixtures of these in varying degrees of purity, i.e., R12/R22; R12/R134A; and R22/R134A. Data are also stored for mixtures of single species refrigerant with air and pump lubricants.

The two resonance center frequencies $f_1$, $f_2$ and two quality figures $Q_1$, $Q_2$ are used to determine the effective mass, $m'$, and these are compared with stored data for each of the possible refrigerants R12, R134A, R22 in all of their possible ranges of mixtures. The resonant frequency data alone may provide somewhat ambiguous data, that is, pure R134A may have the same resonance frequency as a specific mixture of refrigerants R12 and R22. To resolve this ambiguity, the effective mass is computed and compared with the ranges of effective masses for pure R134A and R12/R22 mixtures. A match on one or the other of these will produce an unambiguous identification of the refrigerant as either pure R134A or impure R12 contaminated with R22.

The entire process of frequency sweeping, computing, comparing, and indicating the result takes only about thirty seconds.

Figure 3:
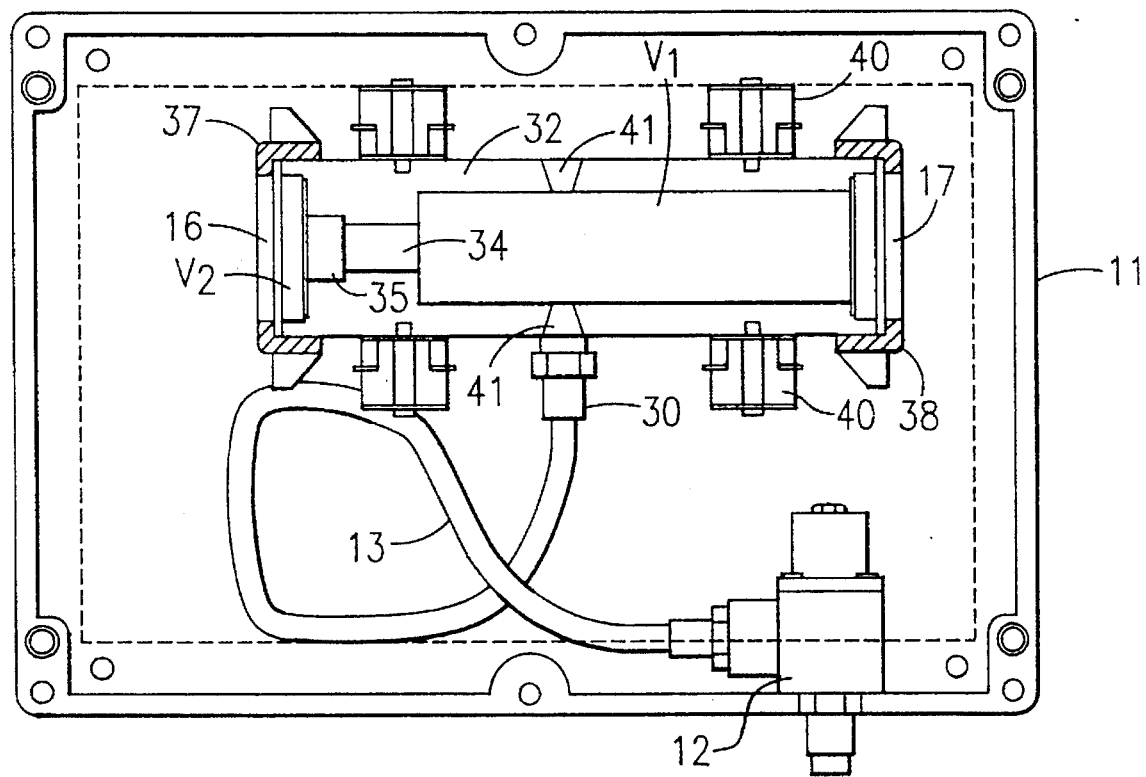
FIG. 3 is a plan view of one practical embodiment described herein showing the acoustic chamber in cross section, and with a front cover removed from the housing thereof.

FIG. 3 illustrates a practical embodiment of this device 10, in which the housing 11 is here shown with a cover removed to expose its interior. Also, electronic elements and connections are omitted here but would be connected generally as shown in FIG. 1. The pressure regulator 12 has a nipple that penetrates the housing, and is connected by the line 13 to a fitting 30 that connects onto the resonator 14.

In this case, the resonator 14 is in the form of an aluminum cylinder 31 in which there are large axial bores 32 and 33 that create the respective volumes $V_1$ and $V_2$. A series of narrower bores 34 and 35 create the resonator necks 25 and 26. A pair of end caps 37 and 38 screw on to threads on the ends of the cylinder 31 to retain the microphones 16, 17.

Vibration-damping mountings 39 and 40 are fitted to the base of the housing 11 and to the cylinder 31 to mount the same in the housing, and at the same time to isolate the resonator from environmental noise.

There are a pair of opposed receptacles 41, 41 in the cylinder 31, with the fitting 30 being mounted into one and the thermal sensor (not shown here) being fitted into the other.

Figure 4:
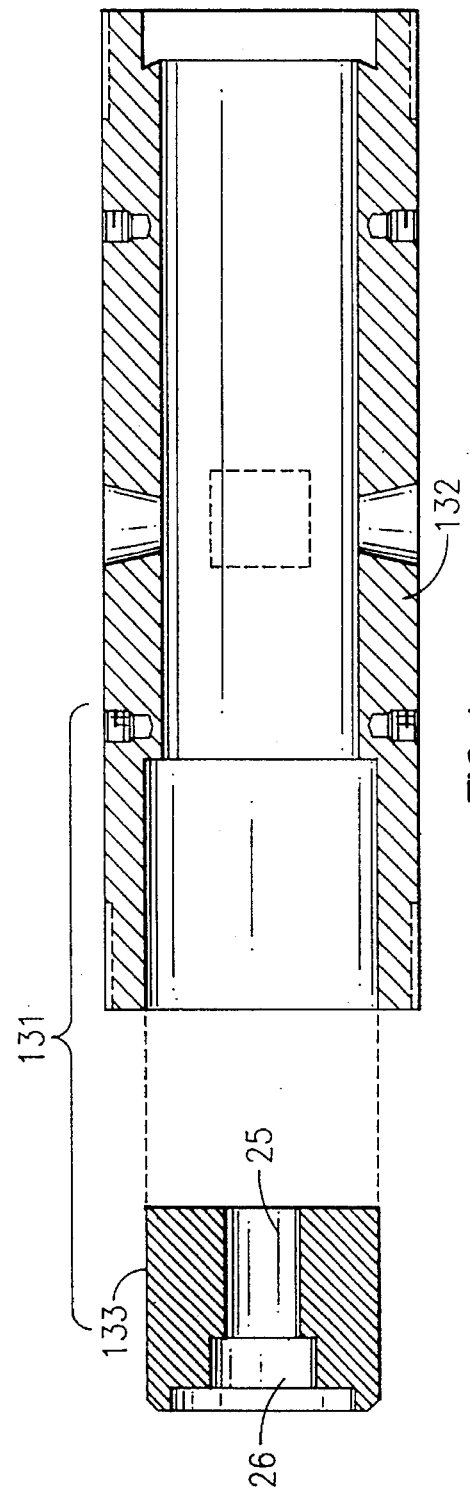
FIG. 4 is a partial exploded view of an alternative two-part construction of the acoustic chamber.

In a variation of this embodiment, a two-piece cylinder 13 is employed for the resonator, as shown in the exploded partial view of FIG. 4. Here the cylinder comprises an outer sleeve 132 and an inner cylindrical plug 133. The plug 133 contains the two necks or smaller bores. This arrangement can be somewhat simpler to machine and manufacture in large quantities. The plug 133 can be made of a different material from that of the outer sleeve 132, e.g., molded of a durable plastic resin.

Returning to FIG. 3, the regulator 12 should have the following characteristics. The regulator should accommodate a vacuum purge (29 inches Hg) of the resonator through the inlet nipple. The regulator valve must accommodate all conventional refrigerants and their lubricants over a range of pressure from 35 psig to 500 psig. On the controlled side, i.e., at the resonator 14, the regulator should have a reproducability of 0.25 psi, and produce a regulated pressure of 2.25 psig. Because the refrigerant can be taken from the system 22 at any of various points in its refrigeration cycle, the regulator is operable over a temperature range of −40° F. to 185° F., and up to 750 psig pressure.

The microphones 16, 17 or other acoustic transducers should be selected to have their natural resonances well above the sweep frequency range, i.e., well above 3 KHz.

In alternative embodiments, the pressure within the resonator 14 can be measured rather than regulated, and the algorithm can compensate for the effect of pressure variations on the resonances.

In some possible embodiments, a Helmholtz resonator or other resonator can provide for a single resonance only, while in still other possible embodiments the resonator can provide for three or more resonances.

Figure 5:
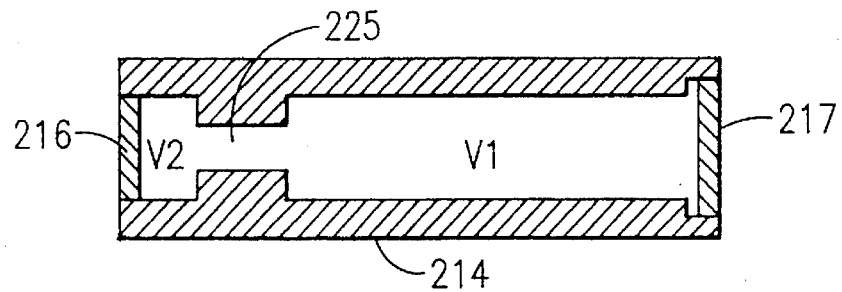
FIG. 5 is a schematic view of a resonator that can be employed in an alternative embodiment.

One simplified embodiment can be explained with respect to FIG. 5 which shows a single resonance Helmholtz resonator 214, with chambers forming volumes $V_2$, $V_1$ and a single neck 225 separating the two. A pair of microphones 216, 217 or other transducers are disposed in contact with the gas in the resonator 214.

Figure 6:
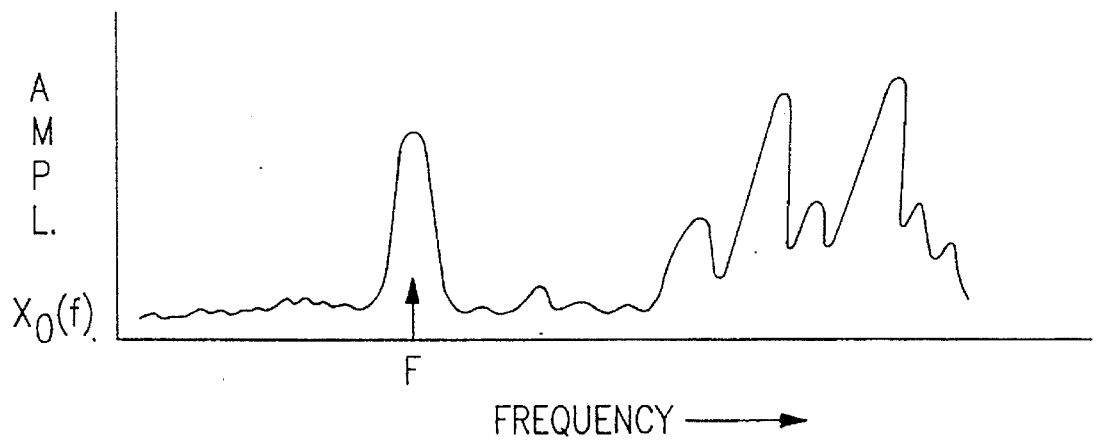
FIG. 6 is a frequency response chart showing a Helmholtz resonance provided by a configuration described herein.

This configuration provides a single Helmholtz resonance F as shown on the chart of FIG. 6.

It should be noted that while the amplitude $X_o(f)$ at any given frequency of vibrations in the chamber is not directly observed, the oscillators create pressure deviations which create microphone output voltages y(f) on the second transducer 16. This output voltage is proportional to the amplitude; $y(f)=K*X_o(f)$, where K is a microphone gain factor.

The gain factor K can be derived by taking a measurement at a frequency far below the resonance F. In this example, a frequency f=333 Hz is used. This step makes the operation of the device independent of microphone characteristics, which can vary from one device to another and can also vary as the microphone ages.

Figure 7:
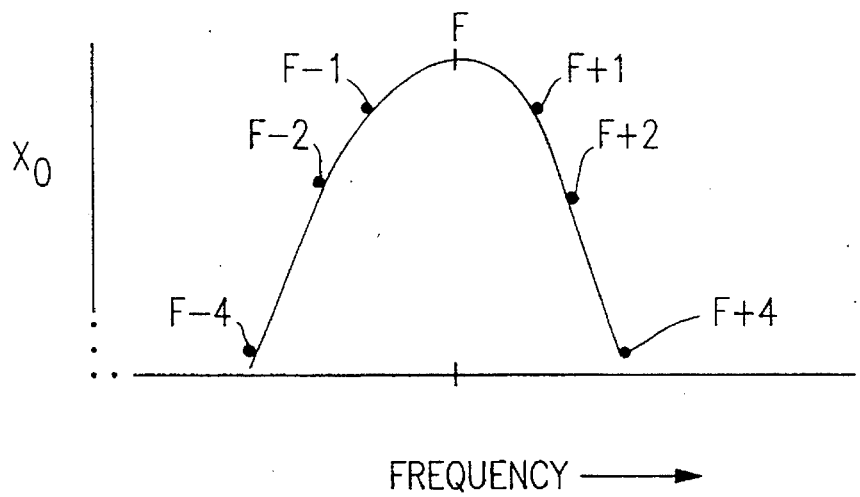
FIG. 7 is a chart showing acoustic response over a small range of frequencies in the vicinity of a resonance peak.

The measurement steps for finding the resonance frequency F, quality factor Q, and equivalent mass m' for a given sample can be carried out as follows:

First the frequency generator is swept between about 600 Hz and 1500 Hz to locate the resonance peak F approximately. Then a careful measurement is made in the neighborhood of the peak to derive the location of the resonance peak F within about 0.5 Hz. A number of measurements of amplitude $X_o(f)$ and frequency $X_o(f)$ are taken for several frequencies at increments above and below the resonance frequency F, as shown generally in FIG. 7. For example, the output level of the microphone 216 is taken for each of the frequencies F, F+1 Hz, F+2 Hz, F+4 Hz, F−1 Hz, F−2 Hz, and F−4 Hz. The factor Q is computed according to the relation:

$$\sqrt{\left(\frac{X_o(F)}{X_o(f)}\right)^2 - 1} = Q|F-f|\frac{2}{F}$$

The several values of Q taken around the resonance are averaged.

Thereafter, the equivalent mass m' of the sample gas is computed, in this example according to the relation:

$$X_o(F) = \frac{A_o/m'}{4\pi^2 F^2} \cdot Q$$

where $A_o$ is the driving frequency amplitude. Each species of refrigerant will have a distinctive pair of values for F and m'.

In a test run of several samples of pure refrigerant and of air, the following results were computed using the test device and method described hereabove:

| Sample | Resonance F (Hz) | Equivalent mass m' |
| --- | --- | --- |
| R134A | 915 | 9.5 |
| R12 | 850 | 13.0 |
| R22 | 1040 | 5.0 |
| Air | 2000 | 2.0 |

For samples of gas mixtures, e.g., R12/R22 mixture, some ambiguity can result if the mixture has the same sound velocity as another species, that is, if the resonance F matches another species resonance. However, this ambiguity can usually be resolved by resorting to other characteristics, such as equivalent mass m'. For example, a blend of R12 and R22 can be selected to have acoustic characteristics similar to R134A, but this blend will have a measurably distinct mass m'. For example:

| Sample | F | m' |
|---|---|---|
| R134A | 915 | 9.5 |
| R12/R22 | 915 | 10.3 |

Thus the device here will automatically distinguish one species from another, and will also distinguish a pure sample from a contaminated sample. The measurements are highly repeatable and reliable.

The Helmholtz resonators that can be employed need not be of the straight, tubular design as shown. For example, the resonator could be a right angle device, such as a tee or elbow. The shape of the resonator can be selected to fit the equipment, or to minimize undesirable resonances.

In addition to the task of identifying samples of refrigerants, the devices can be configured for a feedback and control role. This can be especially useful where two species of a gas must be identified an the blend of the two species must be accurately maintained. For example, the device can be employed in a surgical environment to control a blend of oxygen and anaesthetic being supplied to a patient.

Also, rather than measuring the temperatures of the resonator, means can be incorporated into the device 10 to control and stabilize the temperature.

An acoustic methodology can measure pressure of the inside of the resonator down to about ⅓ atmosphere. This can be used as a check to ensure that the resonator has been purged between samples.

Rather than the lamps L1–L4, many other types of indicators can be employed to indicate the species and quality of the sample gas being tested.

Calibration of the device can be carried out by using a known, available gas, such as shop air, or a standard known refrigerant or refrigerant mixture.

Also, while not specifically shown here, a switch circuit can be included to reverse the roles of the transducers 16, 17 which can increase the reliability of the identification.

The device described hereinabove performs satisfactorily when the refrigerants are pure or cross-contaminated. The technique described above detects the presence of a large air mass, as may be the case if there is a leak in a air conditioning, refrigeration, or heat pump system. However, small quantities of air can cause ambiguities that could be difficult to resolve.

If a small fraction of air is present, e.g. 2% to 20% in refrigerant R12, the air can be mistaken as contamination with another refrigerant R134a. Even though in an ideal system no air should be present, in real-world automotive air conditioning systems a small fraction of air remains when the system is charged. Often the air mass accumulates near the test port, where its effects are most exaggerated. As a result, the technique described hereinabove has difficulty identifying a species unambiguously unless the air is somehow purged from the sample.

The technique of this invention circumvents the air contamination problem in refrigerant gases. The Helmholtz resonator can be operated in a fashion very similar to the previously described technique, to gather additional data that can be used to ascertain the fraction of air that is present in a sample of refrigerant vapor being tested. That is, a secondary physical parameter is derived which varies directly with the quantity of air present. This permits the fraction of air to be computed, and a corrected resonance frequency or frequencies can be found. By using the corrected resonance frequency or frequencies, it is possible to discriminate unambiguously between refrigerants.

As discussed previously, the resonance frequency $F_H$ of a Helmholtz resonator can be expressed as $$F_H^2 = \frac{1}{(2\pi)^2} C_o^2 \frac{A}{vl}$$

or $$F_H = \frac{1}{2\pi} C_o \sqrt{\frac{A}{vl}}$$

where $C_o$ is the speed of sound in the refrigerant sample, and the other terms A, v, and l relate to the geometry of the resonator. All of the geometric factors can be combined:

$$\alpha = \frac{1}{2\pi} \sqrt{\frac{A}{vl}}$$

yielding:

$$F_H = \alpha C_o$$

The speed of sound can be determined from thermodynamic factors, $$C_o = \sqrt{\frac{\gamma P}{\rho}}$$

where $\gamma$ is the specific heat ratio, Cp/Cv, Cp, and Cv are the gas specific heats at constant pressure and at constant volume, respectively, P is the static gas pressure, and $\rho$ is the gas density. It should be understood that of the factors, $\gamma$ is only slightly dependent upon pressure, but 92 is strongly dependent upon pressure.

There is an empirical relationship expressed in Churchill, Practical Use of Theory in Fluid Flow, vol. 1, pp. 10–11 (1980):

$$P/\rho^k = \text{constant or } P = \beta^{2k} * \rho^k$$

Here $\beta^{2k}$ is a proportionality constant and the exponent k is approximately equal to unity for isothermal processes and to $\gamma$ for adiabatic processes.

Combining the above relationships yields $$F_H = \alpha\beta \sqrt{\gamma P^{(1-1/K)}}$$

or $$F_H = \alpha\beta \sqrt{\gamma} \times P^{(\frac{k-1}{2k})}$$

This means that for any given species of gas, $F_H$ is independent of pressure if k=1, $F_H$ increases with pressure if k>1, and $F_H$ decreases with pressure if k<1.

Therefore, by finding the derivatives of resonant frequency $F_H$ with respect to pressure P, we can estimate the value of the factor k. Refrigerant gases and the components of air belong to entirely different classes, and have entirely different thermodynamic properties. Thus, as one would expect, the respective values of k are quite different for refrigerants and for air.

In practice, we measure this resonance frequency $(F_H)$ at one pressure $P_1$ (for example, at atmospheric pressure) and call it $F_1$. Similar measurement at another pressure $P_2$ yields a second resonance frequency $F_2$. ($P_2$ may be 5–10 psi above atmosphere).

Then we define a ratio frequency R such that $$R = \frac{F_2}{F_1} = \left(\frac{P_2}{P_1}\right)^{\frac{k-1}{2K}}$$

This equation is derived from the equation just above, ignoring variations in γ due to pressure difference. If $P_2$ is not too far from pressure $P_1$, we can linearize this equation $$R = \left[1 + \frac{(P_2 - P_1)}{P_1}\right]^{\frac{k-1}{2k}} \approx 1 + \left[\left(\frac{k-1}{2k}\right) \cdot \frac{1}{P_1}\right](P_2 - P_1)$$

For these purposes, there is a linear relationship between the frequency ratio and the pressure difference $(P_2-P_1)$, the slope being $((k-1)/P_1) \div 2k$.

We can substitute for a slope factor S, $$S = \left(\frac{k-1}{2k}\right)\frac{1}{P_1} = \frac{1}{2P_1}(1 - 1/k)$$

Thus, the slope S will be different for different gases or classes of gases, because the factor k is different. The linearized relationship is a convenient simplification of a complicated process, but the general result holds sufficiently for a good estimate of the amount of air present.

Experimental measurement of slope for refrigerant R12 and for air respectively yielded the results:

S=−0.001 for R12,

S=+0.0004 for air, the units of S being inverse pressure, (psi)$^{-1}$.

This means that the values of k can be computed both for the refrigerant $R_{12}$ and for air as follows:

| R12 | Air |
|---|---|
| S = −.001/psi | S = 0.0004/psi |
| $P_1$ = 1 atm ≈ 14.7 psi | $P_1$ = 1 atm = 14.7 psi |
| (k − 1) ÷ 2k = −.001 × 14.7 = −.0147 | (k − 1) ÷ 2k = .0004 × 14.7 = .00588 |
| or 1 − 1/k − .0294 | or 1 − 1/k = .01176 |
| or 1/k = 1.0294 | 1/k = .98824 |
| k = 0.9714 | k = 1.0119 |

The pressure is raised from $P_1$ to $P_2$, or lowered from $P_2$ to $P_1$, in a rather slow process, so as to approximate isothermal, rather than adiabatic conditions. For an ideal gas in isothermal transition, k=1. Thus, our results are consistent with generally expected values of k.

Figure 8:
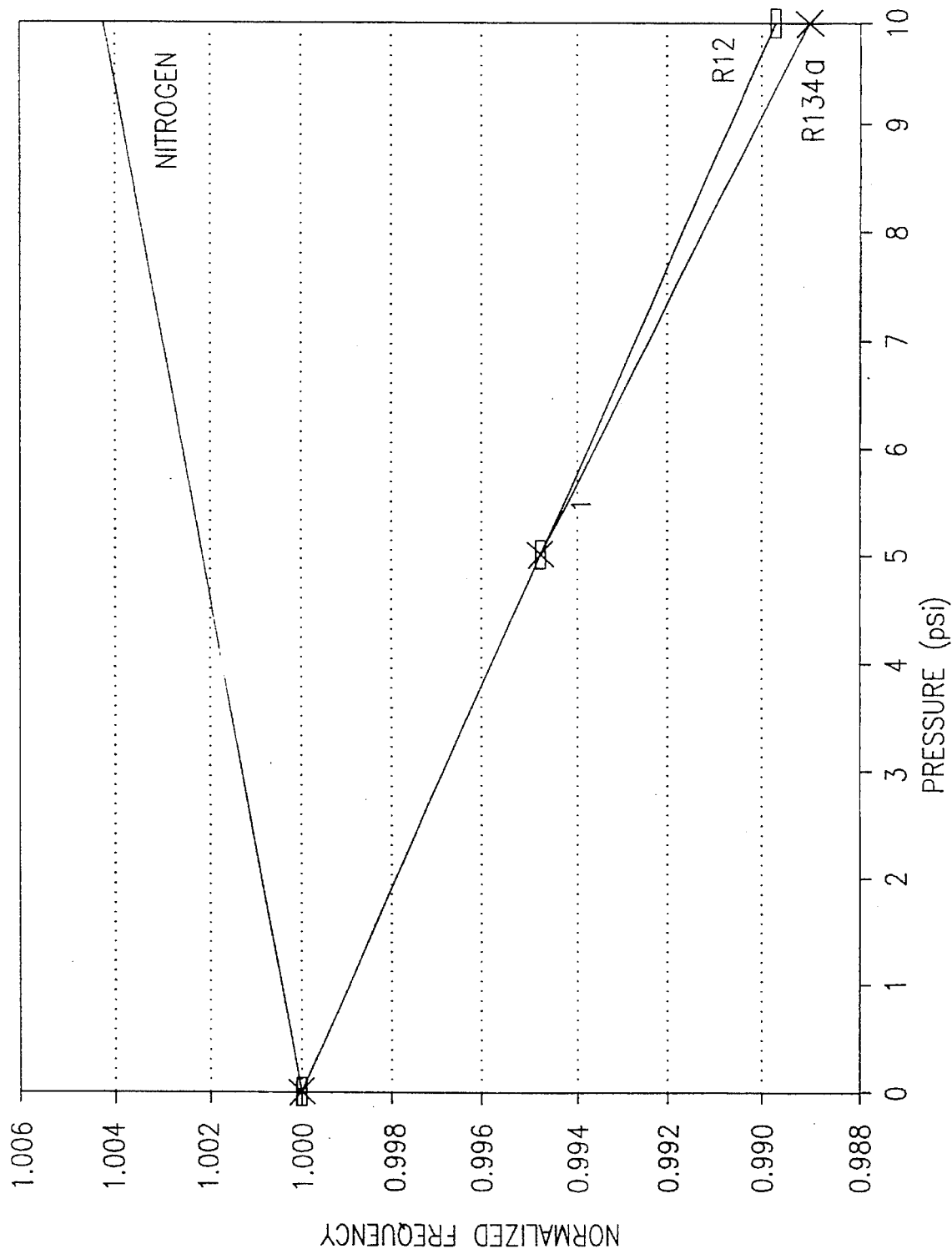
FIG. 8 is a chart showing the relation of normalized harmonic frequency versus pressure for nitrogen and for typical refrigerants.

A chart showing the relation of normalized harmonic frequency versus pressure for nitrogen and for refrigerants R12 and R134a is given in FIG. 8.

In a preferred mode of operation, the test refrigerant vapor is supplied to the Helmholtz resonator 14, filling it initially to a pressure $P_2$ about 10 psi above atmospheric pressure. For this, the regulator 12 is adapted to have first and second stable settings, one being at this pressure $P_2$ and another at a lower pressure $P_1$, for example 2.25 psig. Alternatively, a bleed valve and pressure sensor could be employed. After the gas is stabilized at this pressure $P_2$, the frequency generator 15 and transducers 16, 17 are operated as described previously, and the computer 19 measures a Helmholtz resonance frequency $F_2$ (or pair of frequencies) at this pressure $P_2$. This resonance frequency value is stored. Then, the valve 21 is opened to permit gas to be evacuated slowly from the cell 14 until the lower pressure $P_1$ is reached. Then the Helmholtz resonance frequency $F_1$ is measured at this lower pressure.

This value is also stored in the computer. Then, the slope S of a normalized frequency versus pressure curve is computed as $$S=(F_2/F_1-1)\div(P_2-P_1),$$

giving a value of S that is specific to the species of gas or mixture of gases present.

Figure 9:
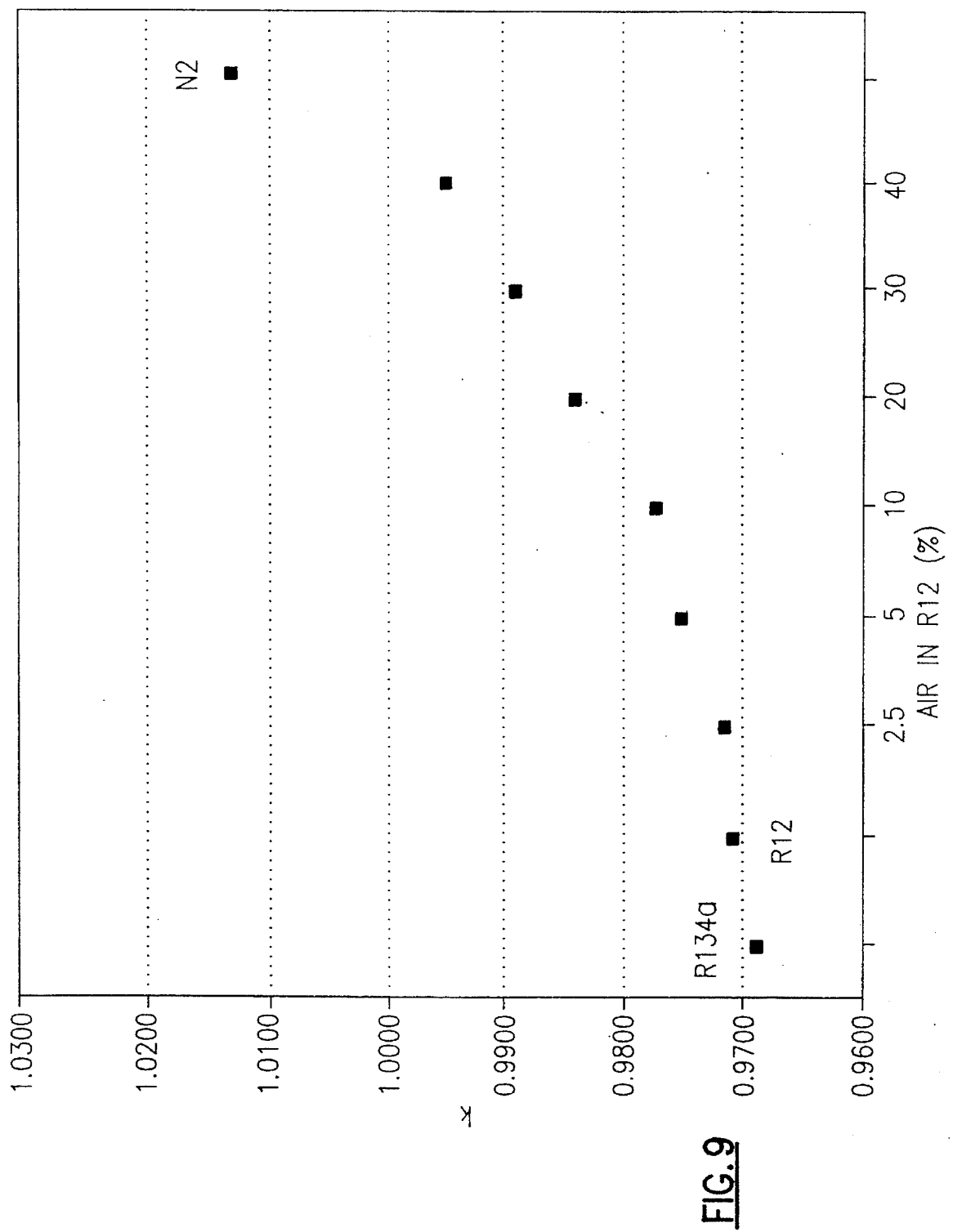
FIG. 9 is a chart showing the relation of gas coefficient k as a percentage of gas present in the refrigerant.

From the slope S, a value of k can be computed, which can be compared with calibrated values as given, for example in the chart of FIG. 9. From this chart, for a given value of coefficient k, the percentage of air present in the refrigerant can be read. This chart is valid for either refrigerant R12 or R134a, because the behavior of those two species are similar.

Figure 10:
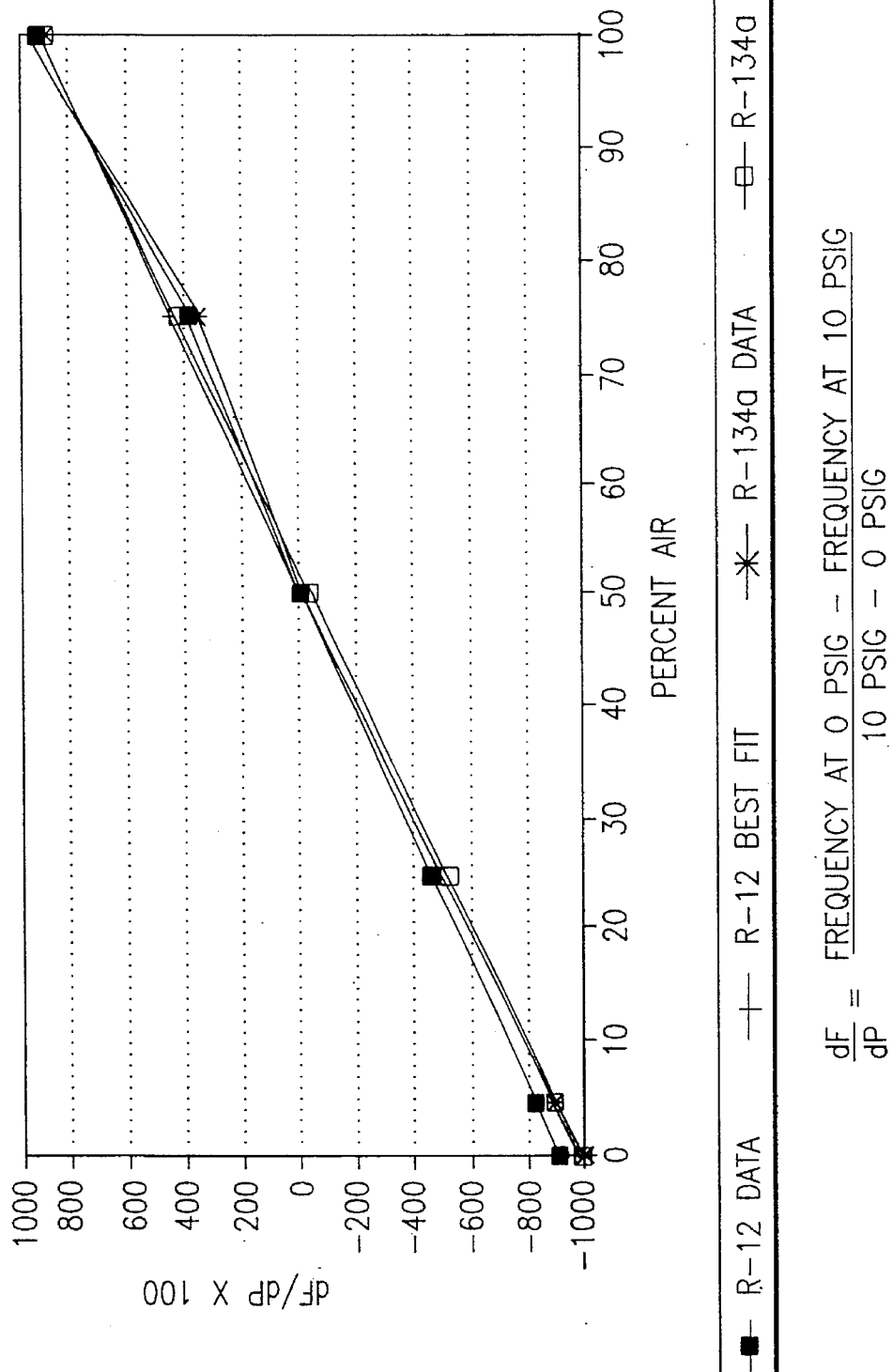
FIG. 10 is a chart showing the relationship of resonant frequency change to change in pressure for mixtures of refrigerant and air.

FIG. 10 is a chart showing the relationship of the pressure rate of change of harmonic frequency dF/dP with percentage of air for mixtures of R12 and air and of R134a and air. The curves for the two refrigerants are both substantially linear and lie very close to one another. Again, it is possible here to derive the percentage of air contamination directly from the frequency rate of change dF/dP, by reference to this or a similar pre-calibrated curve.

Figure 11:
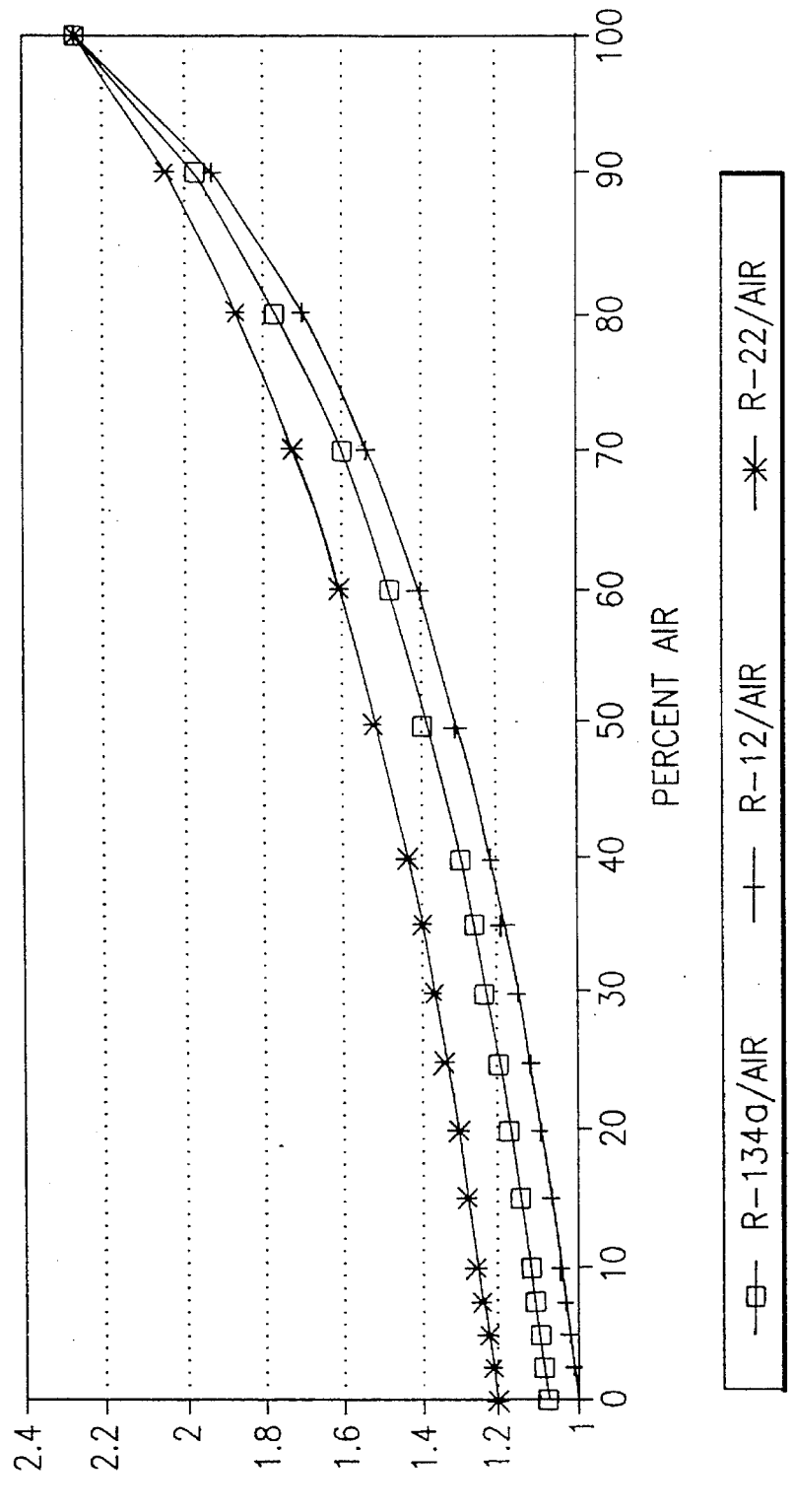
FIG. 11 is a calibration chart for determining a resonant frequency correction factor as a function of air mass present in the refrigerant.

Once the quantity of air in the sample has been determined, a frequency correction factor ΔF/F can be obtained from another pre-calibrated curve such as is shown in FIG. 11.

FIG. 11 shows a plot of normalized frequency for each refrigerant R12, R22 and R134a (relative to pure R12) as a function of percentage of air in the sample. This data provides a correction factor ΔF that is to be added to the fundamental resonance frequency to provide a corrected resonance frequency $F_1+\Delta F$. From this value, a corrected resonance F, or a pair of upper and lower corrected resonances, are computed. The values of Q and m' can be computed, as described previously. These corrected values, with the presence of air mass factored out, permit unambiguous identification of refrigerant species, and can reliably distinguish pure from contaminated refrigerant.

This technique can also be employed to identify species other than refrigerants, i.e. gases such as methane, propane, or butane, in which a gas may be present. The other gas present can be air or can be another gas or mixture of a class different from the main species of interest.

While this invention has been described in terms of a preferred embodiment, it is clear that the invention is not limited to that embodiment. Rather, many possible modifications and variation would present themselves to persons skilled in the art without departing from the scope and spirit of this invention, as defined in the appended claims.

I claim:

1. A process of acoustically testing a refrigerant vapor to determine the content of air present in the refrigerant vapor, comprising the steps of:

injecting a quantity of the refrigerant vapor to be tested into a resonant test cell so that the vapor therein is at one known pressure;

driving an oscillator in communication with said cell over a sweep of frequencies to determine a first principal resonance frequency at said one pressure;

changing the quantity of said refrigerant vapor in said resonant cell so that the vapor therein is at another known pressure;

driving said oscillator over a sweep of frequencies to determine a second principal resonance frequency at said another pressure;

computing a ratio representative of a difference between said first and second resonance frequencies compared with a difference between said one and another pressures; and comparing the computed ratio with a set of precalibrated values to determine the content of air present in said refrigerant.

2. The process of acoustically testing a refrigerant vapor according to claim 1, wherein said ratio computing step comprises the steps of a) calculating a value R, $$R = \frac{F_2}{F_1}$$

wherein $F_2$ and $F_1$ are said first and second resonance frequencies; and b) computing a slope S using a relationship $$R = 1 + S(P_2 - P_1),$$

wherein $P_2$=said one pressure, and $P_1$=said another pressure.

3. The process of acoustically testing a refrigerant vapor according to claim 1, wherein said resonant test cell is a Helmholtz cell having first and second predetermined volumes separated by a neck passageway of predetermined cross sectional area and length.

4. The process of acoustically testing a refrigerant vapor according to claim 3, wherein said oscillator means includes a transducer in acoustic contact with one of said first and second volumes.

5. A process of determining the species and purity of an unknown gaseous substance of a given class in which another class of gaseous substance may be present, comprising the steps of:

introducing said substance in vapor phase into a resonant test cell so that the vapor therein is at one known pressure;

driving an oscillator in communication with said cell over a sweep of frequencies to determine a first principal resonance frequency at said one pressure;

changing the quantity of said refrigerant vapor in said resonant cell so that the vapor therein is at another known pressure;

driving said oscillator over a sweep of frequencies to determine a second principal resonance frequency at said another pressure;

providing an output signal representative of strength of acoustic vibrations in said chamber over said sweep of frequencies at one of said one pressure and said another pressure;

determining, based on said output signal, a center frequency for a corresponding one of said first and second resonance frequencies;

determining, based on said output signal, a sharpness factor for said corresponding one of said first and second resonance frequencies;

computing a ratio representative of a difference between said first and second resonance frequencies compared with a difference between said one and said another pressures;

comparing the computed ratio with a set of precalibrated values to determine the content of said another class of gaseous substance present in said unknown gaseous substance;

computing a corrected resonance center frequency by combining said center frequency with a calibrated value that is based on the content of the another class of gaseous substance present in the unknown gaseous substance; and comparing data based on said sharpness factor with known data to identify the species and purity of said unknown gaseous substance.

* * * * *